(12) United States Patent
Martin et al.

(10) Patent No.: US 12,648,767 B2
(45) Date of Patent: Jun. 9, 2026

(54) SURGICAL SYSTEM AND DEVICE

(71) Applicant: Thompson Surgical Instruments, Inc., Traverse City, MI (US)

(72) Inventors: Christopher T. Martin, Empire, MI (US); Josh Delickta, Elk Rapids, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 82 days.

(21) Appl. No.: 18/668,415

(22) Filed: May 20, 2024

(65) Prior Publication Data

US 2024/0390036 A1 Nov. 28, 2024

Related U.S. Application Data

(60) Provisional application No. 63/468,101, filed on May 22, 2023.

(51) Int. Cl.

| | |
|---|---|
| ***A61B 17/02*** | (2006.01) |
| ***A61B 17/56*** | (2006.01) |
| ***A61B 17/60*** | (2006.01) |
| ***A61B 17/64*** | (2006.01) |
| ***A61B 17/66*** | (2006.01) |
| *A61B 17/00* | (2006.01) |

(52) U.S. Cl.

CPC .......... *A61B 17/0281* (2013.01); *A61B 17/56* (2013.01); *A61B 17/60* (2013.01); *A61B 17/6433* (2013.01); *A61B 17/66* (2013.01); *A61B 2017/00407* (2013.01)

(58) Field of Classification Search

CPC ..... A61B 17/02; A61B 17/0281; A61B 17/60; A61B 17/6408; A61B 17/6433; A61B 17/66; A61B 2090/571; A61G 13/101; A61G 13/122

See application file for complete search history.

(56) References Cited

U.S. PATENT DOCUMENTS

| | | | | |
|---|---|---|---|---|
| 5,897,490 A * | 4/1999 | Fox | A61B 17/02 | 600/232 |
| 5,908,382 A * | 6/1999 | Koros | A61B 17/0206 | 600/232 |
| 5,984,867 A * | 11/1999 | Deckman | A61B 17/0206 | 600/231 |

(Continued)

FOREIGN PATENT DOCUMENTS

| | | | |
|---|---|---|---|
| CN | 103932744 A * | 7/2014 | A61B 17/0281 |

OTHER PUBLICATIONS

"Sternal Elevation by the Crane Technique During Pectus Excavatum Repair: A Quantitative Analysis", Erik R. de Loos, et al., JTCVS Techniques c vol. 9, No. C, 9 pages, 2021.

*Primary Examiner* — Larry E Waggle, Jr.

(74) *Attorney, Agent, or Firm* — McAndrews, Held & Malloy, Ltd.

(57) ABSTRACT

A surgical device includes a carriage, a rack, a clamp, a lifter plate, and a ratchet. The rack passes through the carriage. The clamp secures the carriage to an object that passes through a passage of the clamp. The lifter plate is coupled to a first end of the rack. The ratchet provides ratcheted movement of the carriage along the rack. The ratcheted movement draws the lifter plate coupled to the first end of the rack toward the carriage.

20 Claims, 8 Drawing Sheets

(56) References Cited

U.S. PATENT DOCUMENTS

| | | | | |
|---|---|---|---|---|
| 6,102,854 A * | 8/2000 | Cartier | ............... | A61B 17/0206 600/210 |
| 7,270,632 B2 * | 9/2007 | Santilli | .................. | A61B 17/02 600/230 |
| 2022/0117593 A1 * | 4/2022 | Carlo, III | ........... | A61B 17/1775 |

* cited by examiner

SURGICAL SYSTEM AND DEVICE

RELATED APPLICATIONS

This application claims benefit and priority to U.S. Provisional Patent Application No. 63/468,101, filed May 22, 2023, the contents of the above-identified application is hereby incorporated herein by reference in its entirety.

BACKGROUND OF THE INVENTION

The present invention relates to systems and devices used during surgical procedures.

*Pectus excavatum* is a structural deformity of the anterior thoracic wall in which the sternum and rib cage are abnormally shaped and produce a caved-in or sunken appearance of the chest. Such an abnormally shaped sternum and rib cage may impair cardiac and respiratory function and may cause pain in the chest and back.

The Nuss surgical procedure has been developed to treat *Pectus excavatum*. The Nuss surgical procedure involves, among other things, elevating the sternum using the "crane technique." In general, the crane technique utilizes a system of surgical devices that attach to and lift the sternum.

*Pectus carinatum* is also a structural deformity of the anterior thoracic wall. Where *Pectus excavatum* produces a caved-in or sunken appearance to the chest, the sternum and rib cage in *Pectus carinatum* protrude abnormally outward. Such outward protrusion of the sternum and rib cage may prevent the heart and lungs from functioning optimally. Thus, individuals with *Pectus carinatum* may experience decreased stamina, shortness of breath, and fatigue. Surgical procedures used to treat *Pectus carinatum* may involve a system of surgical devices that compress the sternum.

Limitations and disadvantages of conventional and traditional approaches should become apparent to one of skill in the art through comparison of such systems with aspects of the embodiments set forth in the remainder of the present disclosure.

BRIEF SUMMARY OF THE INVENTION

Surgical systems and devices are shown in and/or described in at least one figure of the present disclosure. Such surgical systems and/or devices of the present disclosure are set forth more completely in the claims. Advantages, aspects, novel features, as well as, details of illustrated embodiments may be more fully understood from the following description and figures.

For at least some embodiments, the surgical system and surgical device are drawn to scale in the above figures.

DETAILED DESCRIPTION OF THE INVENTION

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three element set {(x), (y), (x, y)}. In other words, "x and/or y" means "one or both of x and y." As another example, "x, y, and/or z" means any element of the seven element set {(x), (y), (z), (x, y), (x, z), (y, z), (x, y, z)}. In other words, "x, y and/or z" means "one or more of x, y, and z." Similarly, as utilized herein, "or" means any one or more of the items in the list joined by "or".

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, or components, but do not preclude the presence or addition of one or more other features, integers, steps, operations, elements, components, or groups thereof.

It will be understood that, although the terms first, second, etc. may be used herein to describe various elements, these elements should not be limited by these terms. These terms are only used to distinguish one element from another element. Thus, for example, a first element, a first component, or a first section discussed below could be termed a second element, a second component, or a second section without departing from the teachings of the present disclosure. Similarly, various spatial terms, such as "upper," "lower," "lateral," "side," "top," "bottom," and the like, may be used in distinguishing one element from another element in a relative manner. It should be understood, however, that components may be oriented in different manners, for example a component may be turned sideways so that its "top" surface is facing horizontally and its "lateral" or "side" surface is facing vertically, without departing from the teachings of the present disclosure.

Figure 1:
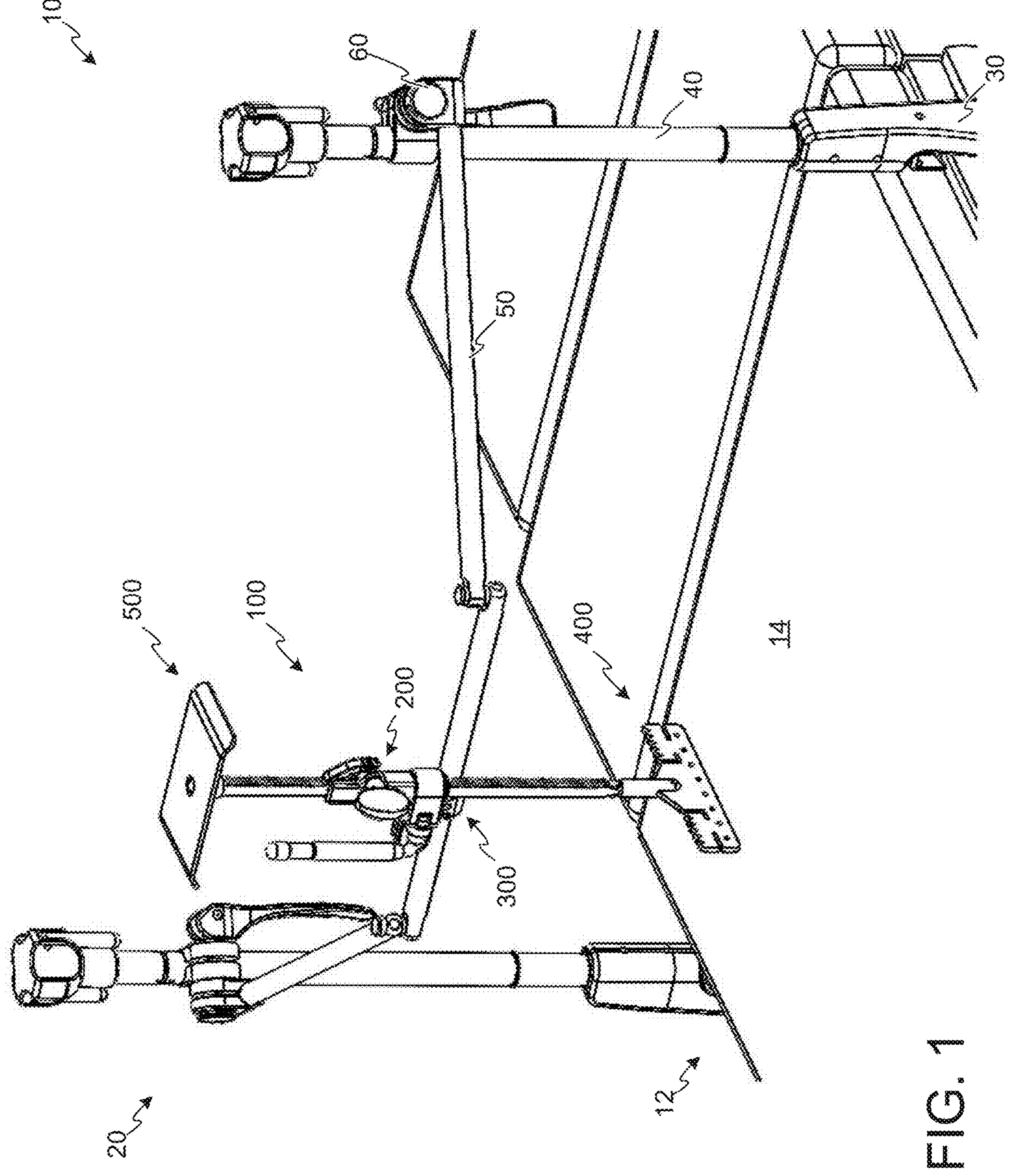
FIG. 1 provides a perspective view for a surgical system comprising a surgical device in which its lifter plate is positioned toward a surgical table.
Figure 2:
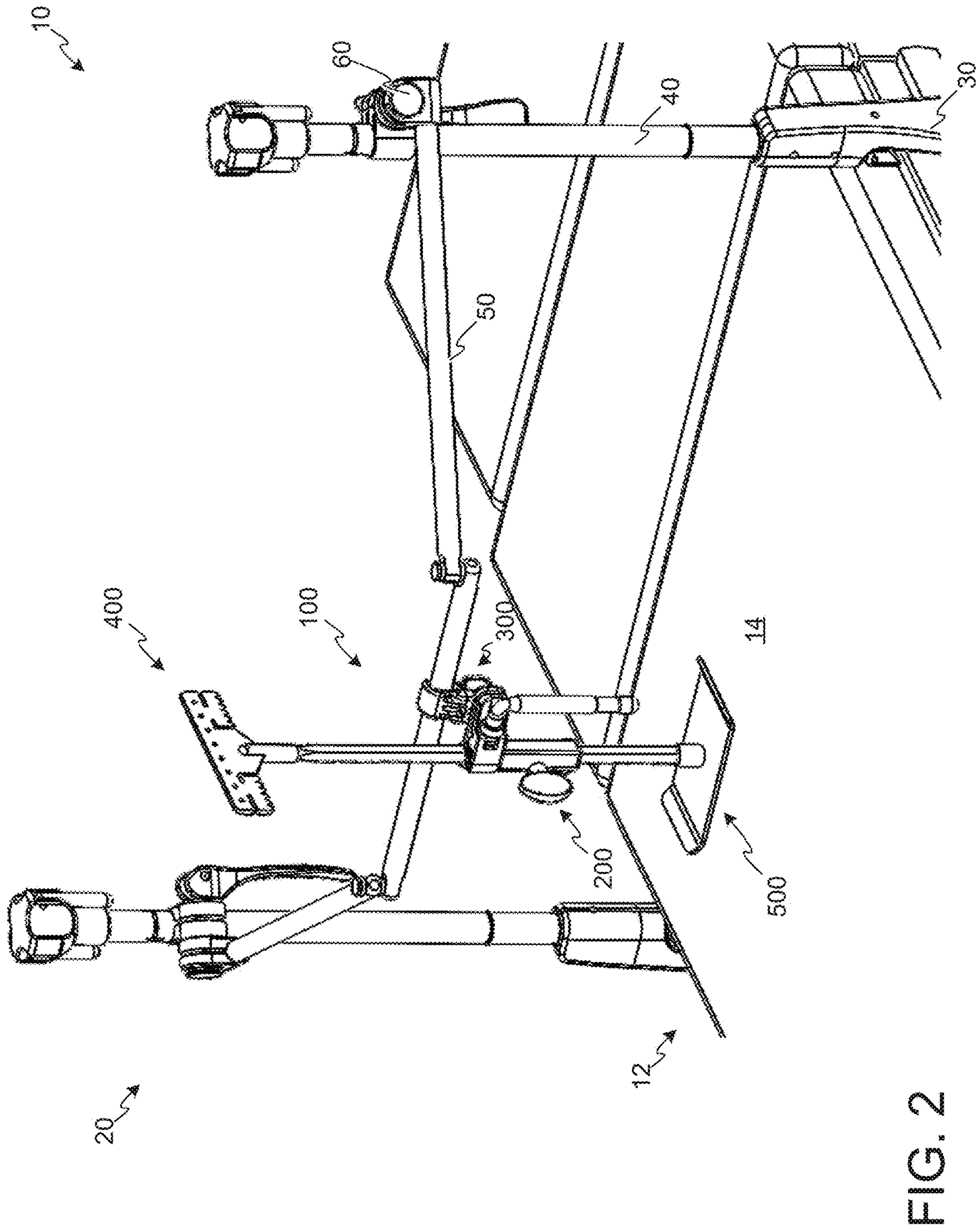
FIG. 2 provides a perspective view for the surgical system of 1 in which the surgical device is positioned with its pusher plate toward the surgical table.

A surgical system 10, which may be used in the treatment of *Pectus excavatum* or *Pectus carinatum*, is shown in FIGS. 1 and 2. In particular, FIG. 1 depicts the surgical system 10 and its surgical device 100. The surgical device 100 is depicted with its lifter plate 400 positioned toward a surgical table 12. Such a configuration may be suitable for treatment of *Pectus excavatum*. Conversely, FIG. 2 depicts the surgical device 100 with its pusher plate 500 positioned toward the surgical table 12. Such a configuration may be suitable for treatment of *Pectus carinatum*.

In particular, the surgical system 10 may include the surgical table 12, a frame assembly 20, and the surgical device 100. The frame assembly 20 may secure the surgical device 100 to the surgical table 12 and may permit positioning the surgical device 100 with respect to an anterior chest wall of a patient lying on the surgical table 12. To this end, the frame assembly 20 may include rail clamps 30, posts 40, a crossbar 50, and joint clamps 60. The rail clamps 30 may be secured to opposite lateral sides of the surgical table 12. A post 40 may extend vertically from each rail clamp 30 and may provide support for the crossbar 50. The joint clamps 60 may secure opposite ends of the crossbar 50 to a respective post 40 such that the crossbar 50 laterally traverses an upper surface 14 of the surgical table 12. Further, the surgical device 100 may be coupled to the crossbar 50 such that either the lifter plate 400 or the pusher plate 500 of the surgical device 100 is positioned toward an upper surface 14 of the surgical table 12.

Joint clamps 60 are shown toward upper ends of their respective posts 40 in FIGS. 1 and 2. However, in various embodiments, the position of the joint clamps 60 may be adjusted along the length of their respective posts 40. Further, in various embodiments, the length of the posts 40 may be adjustable. As such, the height of the crossbar 50 may be adjusted in relation to the upper surface 14 of the surgical table 12 by adjusting the position of the joint clamps 60 along the posts 40 and/or adjusting the length of the posts 40. This positioning of the joint clamps 60 and/or posts 40 may enable a user to position the crossbar 50 and the surgical device 100 coupled thereto at a suitable height for the anatomy of the patient and the surgical procedure to be performed.

Figure 5B:
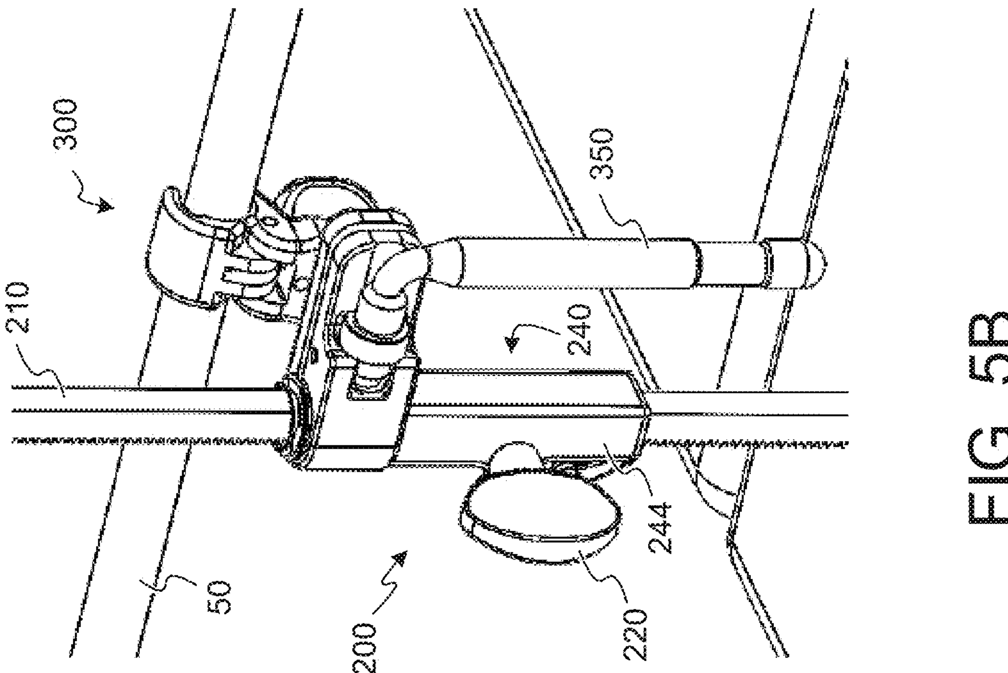
FIGS. 5A and 5B provide perspective views for the ratchet and clamp of the surgical device shown in FIGS. 1 and 2.
Figure 5A:
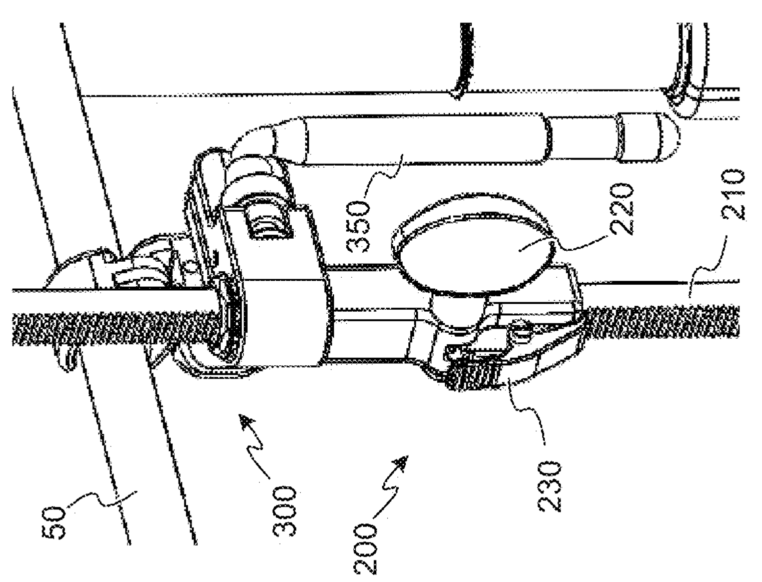
Figure 6:
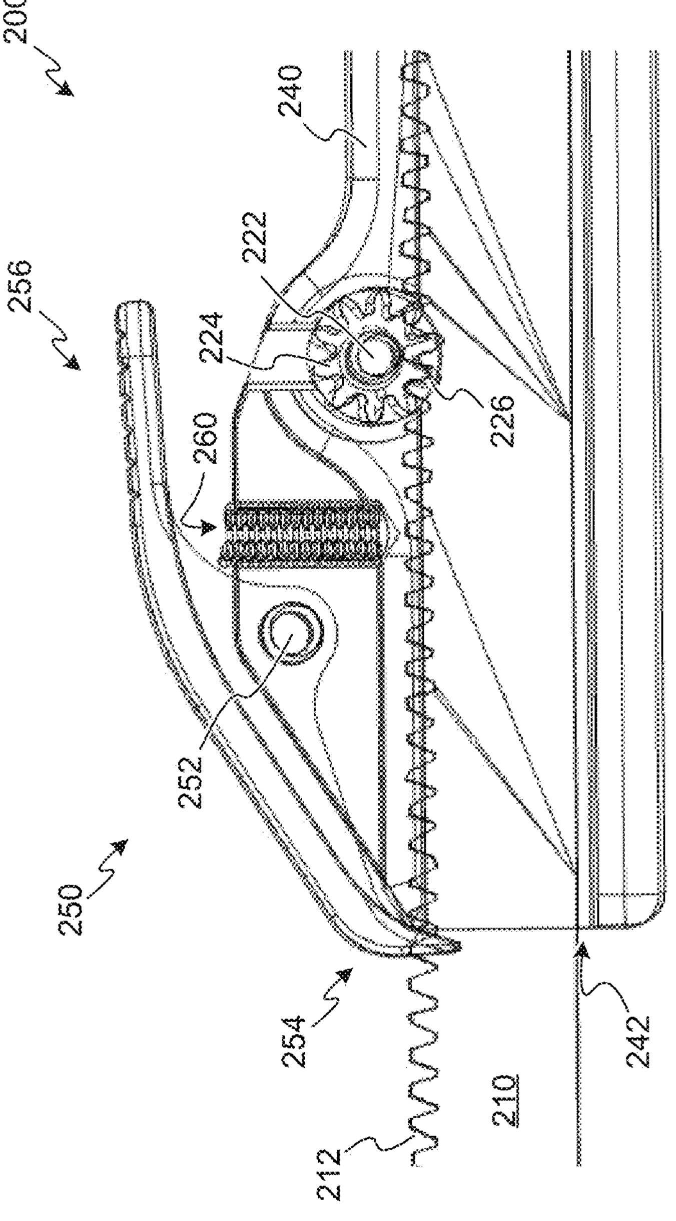
FIG. 6 provides a cross section view for the ratchet of the surgical device shown in FIGS. 1 and 2.
Figure 7A:
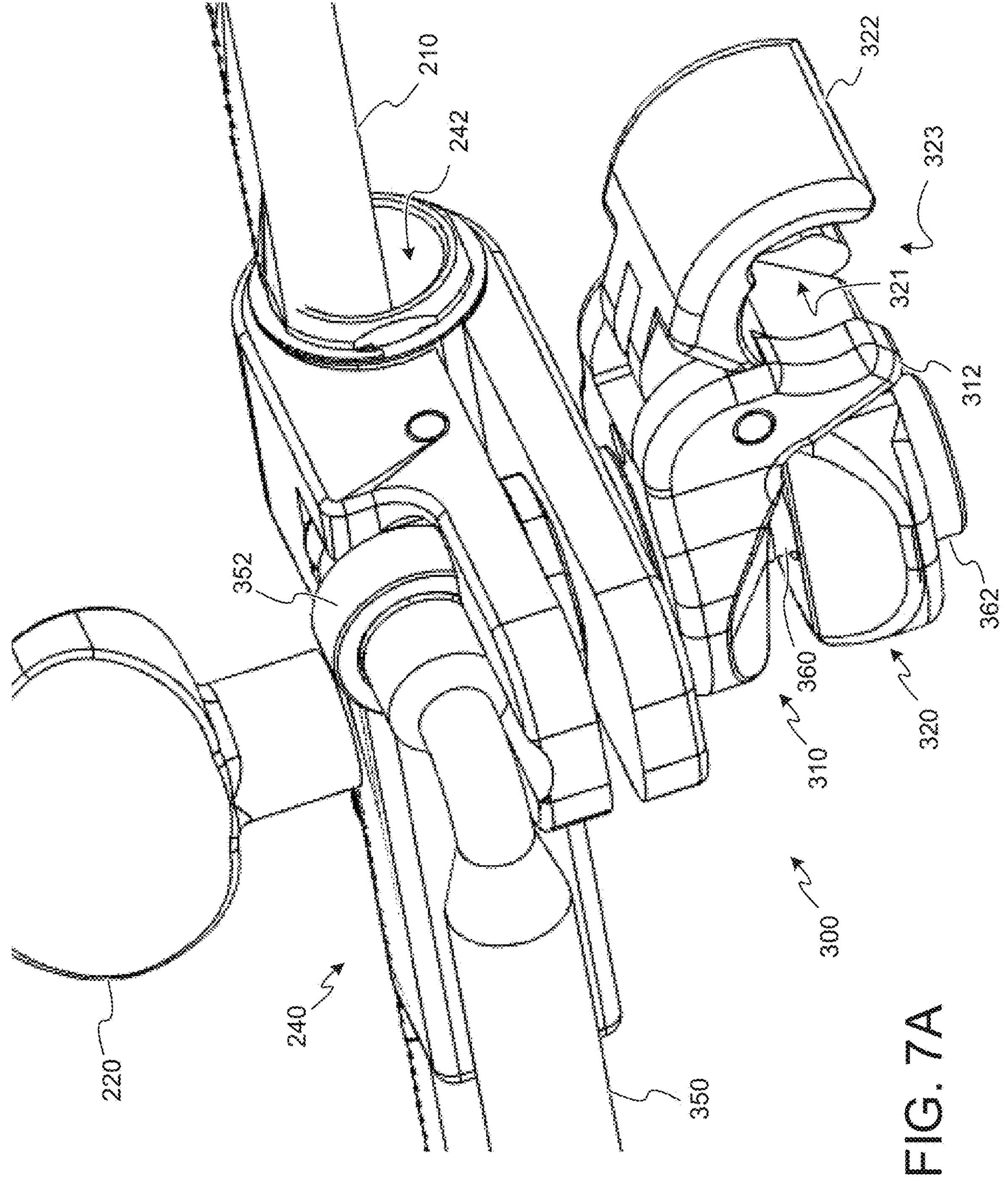
FIGS. 7A-7C provide cross section and perspective views for the clamp of the surgical device shown in FIGS. 1 and 2.
Figure 7B:
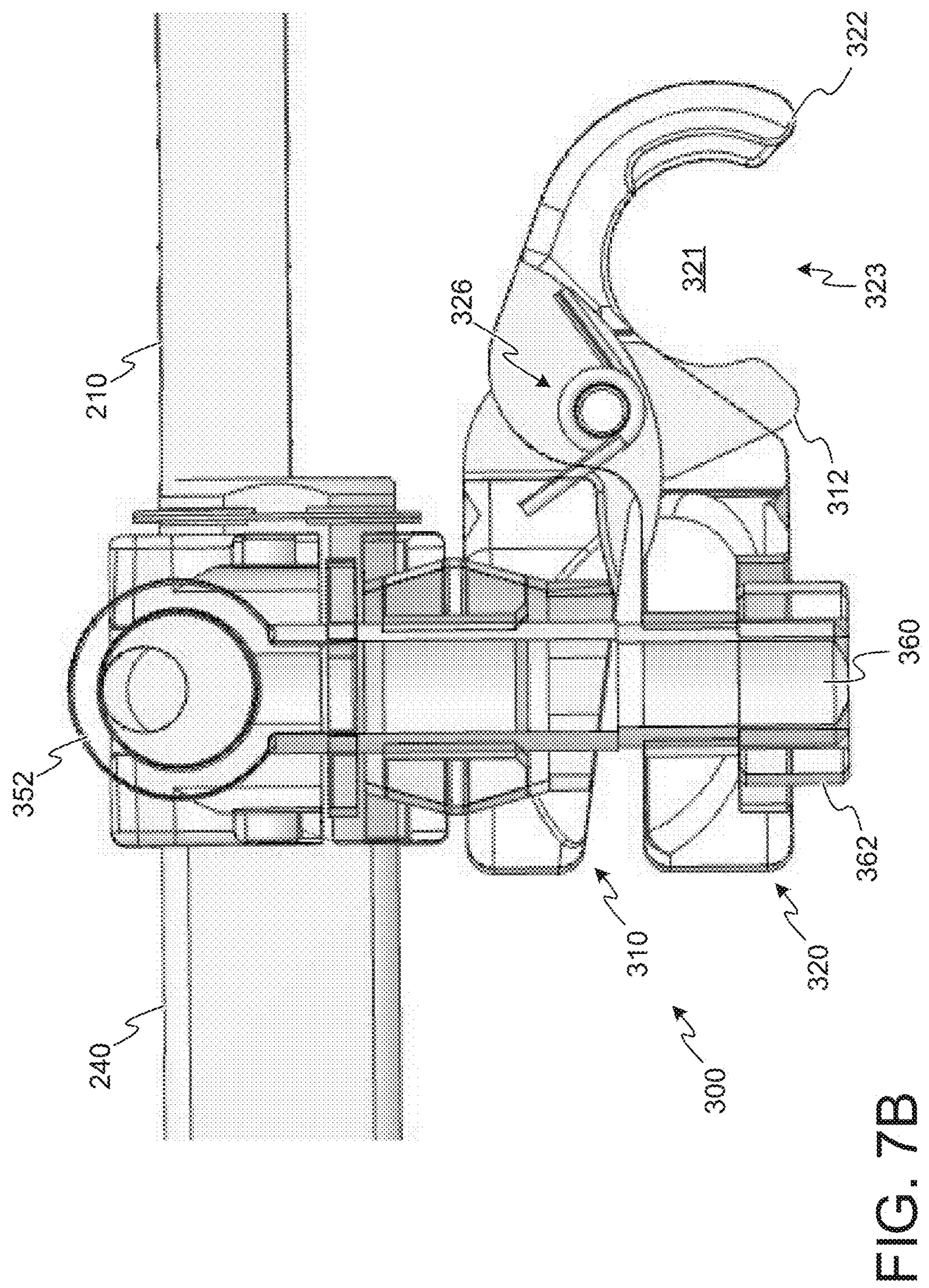
Figure 7C:
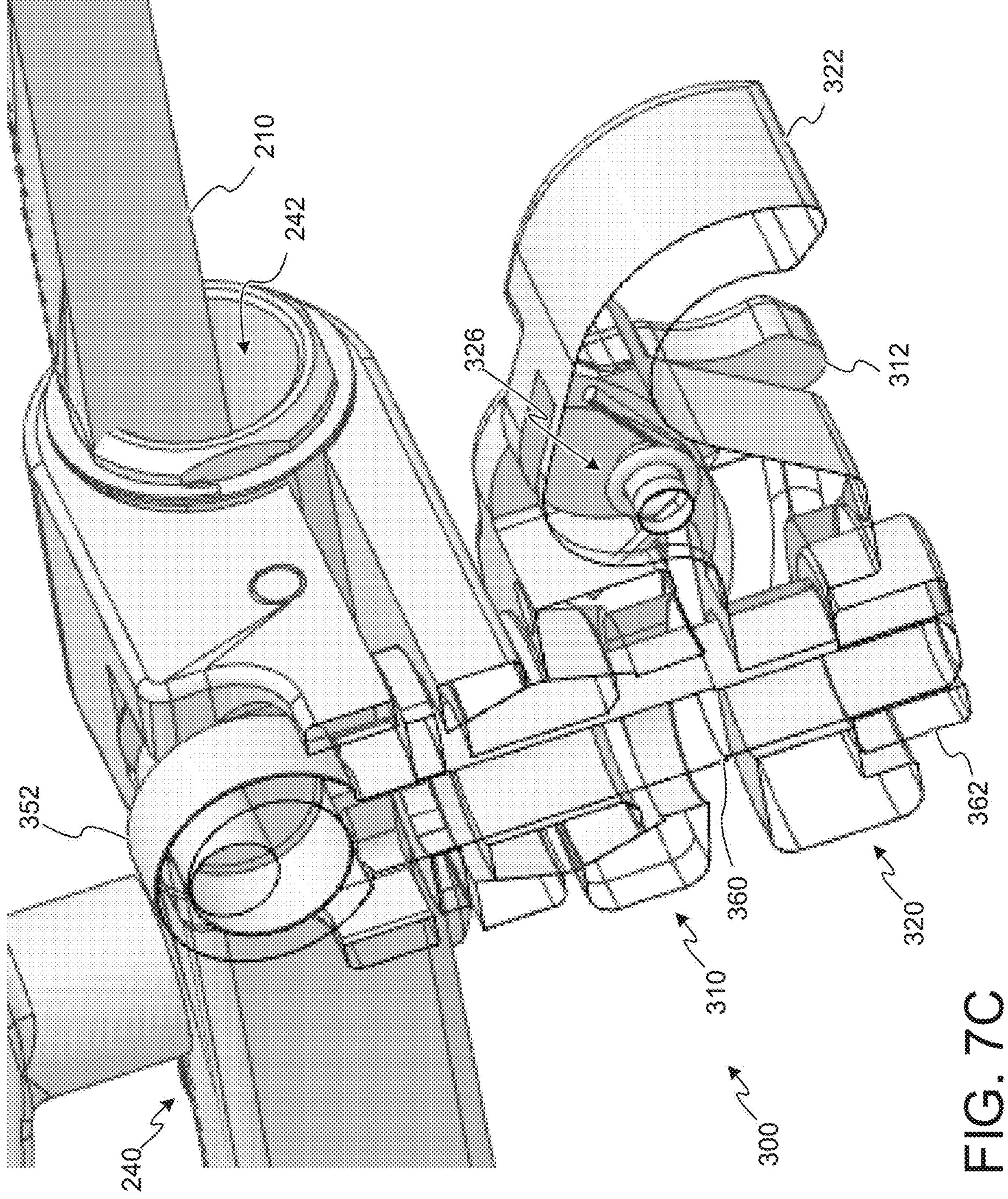

The surgical device 100 may include a ratchet 200, a clamp 300, the lifter plate 400, and the pusher plate 500. Referring now to FIGS. 5A, 5B, and 6, the ratchet 200 may comprise a rack 210 with teeth 212, a handle 220, a carriage 240, and a pawl 250. The rack 210 may pass through a longitudinal channel 242 of the carriage 240. A shaft 222 of the handle 220 may pass through a lateral side 244 of the carriage 240 such that a pinion gear 224 of the shaft 222 engages the teeth 212 of the rack 210. Rotation of the handle 220 thus rotates the pinion gear 224 whose teeth 226 engage the teeth 212 of the rack 210. Rotation of the handle 220 may cause the pinion gear 224 to interact with the teeth 212 of the rack 210 and may cause the carriage 240 to longitudinally traverse along the rack 210.

The ratchet 200 in various embodiments may comprise a pawl 250 coupled to the carriage 240 via a pivot 252 between a pawl distal portion 254 and a pawl proximal portion 256. Moreover, the ratchet 200 may include a spring 260 that biases the pawl proximal portion 256 away from the carriage 240. Such biasing of the pawl proximal portion 256 may cause the pawl 250 to rotate about the pivot 252 and bias the pawl distal portion 254 toward the rack 210. As such, the pawl distal portion 254 may be spring-biased to engage teeth 212 of the rack 210 when no external force is applied to the pawl 250. The pawl 250 and teeth 212 may permit ratcheted movement of the carriage 240 in a first direction away from the pawl distal portion 254 when the pawl distal portion 254 is engaged with the teeth 212. Moreover, while engaged, the pawl 250 and teeth 212 may prevent movement in a second direction that is opposite the first direction.

A user may press the pawl proximal portion 256 with sufficient force to overcoming the biasing force of the spring 260. Due to such force applied to the pawl proximal portion 256, the pawl proximal portion 256 may rotate about the pivot 252 and toward the carriage 240 thus causing the pawl distal portion 254 to rotate about the pivot 252 and away from the rack 210. In this manner, a user may press the pawl proximal portion 256 to disengage pawl distal portion 254 from the teeth 212. When disengaged, the carriage 240 may be moved freely along the rack 210 in first direction and the second direction.

The teeth 212 of the rack 210 in various embodiments may be uniformly-shaped and symmetrically-sloped, with leading and trailing edges having the same slope. However, in some embodiments, the teeth 212 are not uniformly-shaped and/or symmetrically-sloped. In various embodiments, the pawl distal portion 254 may not be symmetrically sloped. Instead, the pawl distal portion 254 may have a leading edge (i.e., edge toward the first direction of ratcheted movement) that is more moderately-sloped than an opposite trailing edge. As a result of the more moderately-sloped or less steeply-sloped leading edge and the positioning of the pivot 252, lateral movement of the carriage 240 in the first direction may impart an upward force upon the pawl distal portion 254 that is sufficient to overcome a biasing force of the spring 260 and rotate the pawl 250 about pivot 252 such that the pawl distal portion 254 may travel over the teeth 212.

Conversely, lateral movement of the carriage 240 in the opposite second direction with respect to the rack 210 may impart a downward force upon the pawl distal portion 254 that rotates the pawl 250 about the pivot 252 such that pawl distal portion 254 moves toward the teeth 212, thus increasing its engagement with the rack 210. In this manner, the pawl 250 may lock or retain the carriage 240 at its position along the rack 210, thereby maintaining a desired position of the lifter plate 400 or the pusher plate 500 with respect to the upper surface 14 of the surgical table 12.

The clamp 300 may secure the carriage 240 to the crossbar 50. Thus, translation of the carriage 240 along the rack 210 may cause the rack 210 to move in relation to the crossbar 50 and the surgical table 12. In particular, turning the handle 220 in the first direction may result in ratcheted movement of the carriage 240 toward the lifter plate 400. However, the pawl 250 may prevent movement of the carriage 240 in the opposite direction (i.e., away from the lifter plate 400) whether via turning the handle 220 or via other forces exerted upon the carriage 240. Thus, when positioned with the lifter plate 400 toward the surgical table 12 as shown in FIG. 1, ratcheted movement of the carriage 240 along the rack 210 may lift the lifter plate 400 and an anterior chest wall, which has been secured to the lifter plate 400, from the surgical table 12. Conversely, when positioned with the pusher plate 500 toward the surgical table 12 as shown in FIG. 2, ratcheted movement of the carriage 240 along the rack 210 may press the pusher plate 500 and an anterior chest wall, which is engaged with the pusher plate 500, toward the surgical table 12.

While the depicted ratchet 200 permits ratcheted movement in a first direction and prevents movement in a second direction, other embodiments may utilize a ratchet that permits ratcheted movement in either direction. Such embodiments generally utilize two pawls in which a first pawl is engaged with the teeth 212 of the rack 210 and a second pawl is disengaged to permit ratcheted movement in a first direction and in which the first pawl is disengaged from the teeth 212 of the rack 210 and the second pawl is engaged with the teeth 212 to permit ratcheted movement in the second direction.

The clamp 300 may be implemented with various types of clamps. For example, the clamp 300 may be implemented similar to the multi-directional joint clamps disclosed in U.S. Pat. No. 11,523,876, which is hereby incorporated by reference in its entirety; similar to the snap joint clamps disclosed in U.S. patent application Ser. No. 17/717,891, which is hereby incorporated by reference; similar to the clip-on joint clamps as disclosed in U.S. Pat. No. 11,633,180, which is hereby incorporated by reference in its entirety; or similar to another type of clamp. In the depicted embodiment, the clamp 300 is implemented similar to the clip-on joint clamp of U.S. Pat. No. 11,633,180.

Referring now to FIGS. 5A, 5B, and 7A-7C, the clamp 300 may include a first scissors portion 310, a second scissors portion 320, a cam lever 350, and a cam bolt 360. The cam bolt 360 may generally passes through cam bolt holes of the first scissor portion 310, and the second scissors portion 320. An upper end of the cam bolt 360 may be coupled to the cam lever 350. A lower end of the cam bolt 360 may be coupled to a base 362.

The cam lever 350 may be rotated between a locked position and an unlocked position. In the locked position, the first scissor portion 310 and the second scissors portion 320 are drawn together and apply a clamping force to an object such as crossbar 50 received between first jaws 312 of the first scissors portion 310 and second jaws 322 of the second scissors portion 320. Conversely, rotating the cam lever 350 from the locked position to an unlocked position increases the distance between a lower surface of the cam head 352 and an upper surface of the base 362, which reduces or removes a compression force. Such change in distance may be due to the rotational axis of the cam head 352 not being coaxial to the center of the cam head 352. See, e.g., FIGS. 7A-7C. Such reduction/removal of the compression force may cause the first scissors portion 310 to move away from the second scissors portion 320 and may reduce or remove forces applied by jaws 312, 322 to the crossbar 50. In particular, the forces applied by the jaws 312, 322 may be sufficiently removed or reduced so as to permit the crossbar 50 to be rotated, slid, or otherwise repositioned within a clamping passage 321 encompassed by the jaws 312, 322.

In some embodiments, the clamp 300 may be imparted with a clip-on feature. In particular, a spring 326 may bias the jaws 312, 322 toward a closed position even when the cam lever 350 is in the unlocked position. While in the unlocked position, an object such as the crossbar 50 may be pressed against a mouth opening 323 between jaws 312, 322 with sufficient force to overcome the biasing force of the spring 326 and expand the mouth opening 323 sufficiently to permit the object to pass between the jaws 312, 322 and into a clamping passage 321. Once passed the jaws 312, 322 and into the clamping passage 321, the spring 326 may bias the jaws 312, 322 back toward the closed position and retain the object in the clamping passage 321.

Conversely, when in the unlocked position, the clamp 300 may be pulled from an object (e.g., crossbar 50) with sufficient force to overcome the biasing force of the spring 326 and sufficiently expand the mouth opening 323 to permit the object to pass between the jaws 312, 322 and out of the clamping passage 321. Again, once passed the jaws 312, 322, the spring 326 may bias the jaws 312, 322 back toward the closed position.

In this manner, the surgical device 100 may be clipped-on the crossbar 50 by pushing the clamp 300 against the crossbar 50 with a clip-on force that overcomes the biasing force of the spring 326, and the surgical device 100 may be removed from the crossbar 50 by pulling the clamp 300 away from the crossbar 50 with a clip-off force that overcomes the biasing force of the spring 326. In certain embodiments, the force of the spring 326 sufficiently biases the jaws 312, 322 toward the closed direction so as to require the clip-off force to be greater than a gravitational force exerted by the surgical device 100 on the clamp 300 when hanging from the crossbar 50. In this manner, the spring 326 and associated clip-off force my prevent the surgical device 100 from detaching from the crossbar 50 due to its own weight when the cam lever 350 is in the unlocked position.

Figures 3, 4:
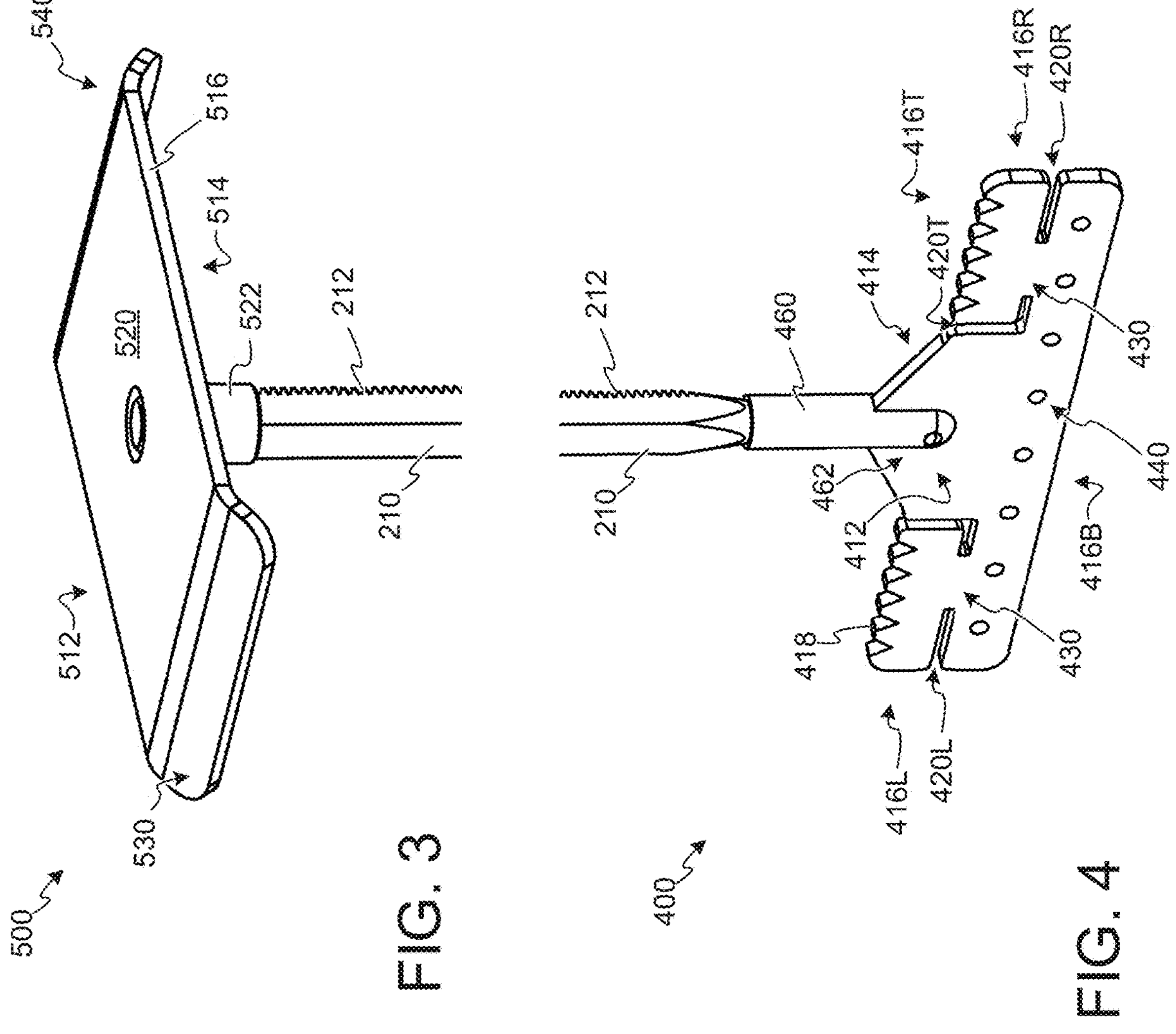
FIG. 3 provides a perspective view for the push plate of the surgical device shown FIGS. 1 and 2.
FIG. 4 provides a perspective view for the lifter plate of the surgical device shown FIGS. 1 and 2.

Referring now to FIG. 4, the lifter plate 400 may comprise a first side 412, a second side 414 opposite the first side 412, and sides 416T, 416B, 416L, 416R adjoining the first side 412 and the second side 414. Lateral side slots 420L, 420R may extend inwardly from the lateral sides 416L, 416R and provide openings that extend through the first side 412 and the second side 414. As depicted, each lateral side slot 420L, 420R may traverse along a respective straight-line path and may provide a uniform width along its straight-line path. Moreover, the straight-line paths of the lateral side slots 420L, 420R may run parallel to the top side 416T or the bottom side 416B or may run perpendicular to a central vertical axis of the lifter plate 400, which is coaxial with a longitudinal axis of the rack 210. Moreover, in the depicted embodiment, the lateral side slots 420L, 420R are collinear. While lateral side slots 420L, 420R are depicted with the above properties, in some embodiments, the lateral side slots 420L, 420R may be curved, multi-segmented, notched, and/or not collinear, and/or may provide non-uninform widths along their respective paths.

As shown, the top side 416T may comprise serrations or teeth 418 for engaging interior surfaces of the anterior chest wall and/or sternum of a patient. The top side 416T may also include top side slots 420T that provide openings that pass through the first side 412 and the second side 414 and extend inwardly from the top side 416T. As depicted, each top side slot 420T may traverse along a respective multi-segment path and may provide a uniform width along its multi-segment path. In particular, each top side slot 420T may run vertical along a first segment from the top side 416T toward a central portion of the lifter plate 400 and horizontally along a second segment from the lower end of its first segment toward a respective lateral side 416L, 416R. Similar to the straight-line paths of the lateral side slots 420L, 420R, the second segments of the top side slots 420T may run parallel to the top side 416T or the bottom side 416B or may run perpendicular to the central vertical axis of the lifter plate 400. Moreover, in the depicted embodiment, the second segments of the top side slots 420T may be collinear with each other and/or collinear with the lateral side slots 420L, 420R. While top side slots 420T are depicted with the above properties, in some embodiments, the top side slots 420T may be curved, a single segment, and/or notched, and/or may provide non-uninform widths along their respective paths.

As shown, terminal ends of the top side slots 420T align with terminal ends of respective lateral side slots 420L, 420R. Such terminal ends may define a spindle 430 their between. Sutures, wires, threads, etc. may be wrapped or spooled around spindles 430 to help anchor the lifter plate 400 to anatomy of the patient. Further, loops formed from sutures, wires, threads, etc. may be passed through slots 420L, 420R, 420T and around the spindles 430 to help anchor the lifter plate 400 to anatomy of the patient.

As further shown, the lifter plate 400 may include one or more holes 440 that extend through the first side 412 and the second side 414. Similar to the slots 420L, 420R, 420T, and spindles 430, sutures, wires, threads, etc. may be passed through the holes 440 to help anchor the lifter plate 400 to anatomy of the patient. FIG. 4 depicts holes 440 uniformly spaced along a straight-line that may run parallel to the top side 416T or the bottom side 416B or that may run perpendicular to the central vertical axis of the lifter plate 400. However, in various embodiments, the holes 440 may be arranged in a non-linear, a non-uniformly spaced, and/or another manner.

The top side 416T of the lifter plate 400 may further include a mount 460. The mount 460 may comprise a hollow cylinder that extends outwardly from the top side 416T. In various embodiments, the diameter the of mount 522 is sized to receive and closely mate with a cylindrical end of the rack 210. In various embodiments, the rack 210 may be affixed to the mount 460 via various techniques such as welding, friction fitting, screws, pins, crimping, etc. that secure the lifter plate 400 to the end of the rack 210 in a fixed configuration. In some embodiments, the mount 460 may include pivot joints, ball joints, and/or other coupling mechanisms 462 which secure the lifter plate 400 to the end of the rack 210 in a manner that permits freedom of movement of the lifter plate 400 about one or more axes with regard to the rack 210. Such freedom of movement may permit the lifter plate 400 to auto-align with anatomy of the patient and potentially reduce tissue trauma as the lifter plate 400 applies a lifting force on interior portions of the anterior chest wall and/or sternum of a patient.

Referring now to FIG. 3, the pusher plate 500 may comprise a first side 512, a second side 514 opposite the first side 512, one or more lateral sides 516 between the first side 512 and the second side 514. In various embodiments, the pusher plate 500 may also comprise a central portion 520, a first flared portion 530, and a second flared portion 540. The first side 512 of the central portion 520 may provide a generally planar surface for engaging an anterior chest wall and/or sternum. The second side 514 of the central portion 520 may include a mount 522. The mount 522 may comprise a hollow cylinder that protrudes from the second side 514. In various embodiments, the diameter the of mount 522 is sized to receive and closely mate with a cylindrical end of the rack 210. In various embodiments, the rack 210 may be affixed to the mount 522 via various techniques such as welding, friction fitting, screws, crimping, etc. that secure the pusher plate 500 to the end of the rack 210 in a fixed configuration. In other embodiments, the mount 522 may include pivot joints, ball joints, and/or other coupling mechanisms which secure the pusher plate 500 to the end of the rack 210 in a manner that permits freedom of movement of the pusher plate 500 about one or more axes with regard to the rack 210. Such freedom of movement may permit the pusher plate 500 to auto-align with anatomy of the patient and potentially reduce tissue trauma as the pusher plate 500 applies force the anterior chest wall and/or sternum.

As shown, the flared portions 530, 540 may extend from opposite lateral sides of the central portion 520. The flared portions 530, 540 may angle and/or curve toward the mount 522, thus providing the first side 512 of the pusher plate 500 with a convex surface. Such angling/curving of the flared portions 530, 540 may soften what would otherwise be an abrupt or sharp transition from the first side 512 to the second side 514 of the pusher plate 500 along its lateral sides 516. Such softening of the transition may reduce tissue trauma, which may result from forces applied by the pusher plate 500 to the anterior chest wall and/or sternum of a patient.

While the foregoing has been described with reference to certain aspects and examples, various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular example(s) disclosed, but that the disclosure includes all embodiments falling within the scope of the appended claims.

What is claimed is:

1. A surgical device, comprising:

a carriage;

a rack that passes through the carriage, wherein the rack comprises a rack first end and a rack second end opposite the rack first end;

a clamp coupled to the carriage and configured to secure the carriage to an object that passes through a passage of the clamp;

a lifter plate coupled to the rack first end;

a ratchet that provides ratcheted movement of the carriage along the rack, wherein the ratcheted movement of the carriage along the rack draws the rack first end and the lifter plate coupled to the rack first end toward the clamp; and a pusher plate coupled to the rack second end; and wherein the ratcheted movement of the carriage along the rack pushes the rack second end and the pusher plate coupled to the rack second end away from the clamp.

2. The surgical device of claim 1, wherein the lifter plate comprises:

a lifter plate first side;

a lifter plate second side opposite the lifter plate first side;

a lifter plate top side coupled to the rack first end; and a plurality of holes that pass through the lifter plate first side and the lifter plate second side.

3. The surgical device of claim 1, wherein the lifter plate comprises:

a lifter plate top side coupled to the rack first end;

a lifter plate bottom side opposite the lifter plate top side;

one or more lifter plate lateral sides between the lifter plate top side and the lifter plate bottom side; and one or more lateral slots that extend into the lifter plate from a respective lifter plate lateral side.

4. The surgical device of claim 3, wherein the lifter plate comprises one or more top slots that extend into the lifter plate from the lifter plate top side.

5. The surgical device of claim 4, wherein the lifter plate comprises one or more spools defined by the one or more lateral slots and the one or more top slots.

6. The surgical device of claim 1, wherein the lifter plate comprises a lifter plate mount that couples the lifter plate to the rack first end and provides freedom of movement of the lifter plate about one or more axes with regard to the rack.

7. The surgical device of claim 1, wherein the lifter plate comprises:

a lifter plate top side coupled to the rack first end; and teeth along the lifter plate top side.

8. The surgical device of claim 1, wherein the pusher plate comprises:

a pusher plate first side coupled to the rack second end;

a pusher plate second side opposite the pusher plate first side; and wherein the pusher plate second side provides a convex surface to engage an anterior chest wall and/or sternum of a patient.

9. The surgical device of claim 1, wherein the pusher plate comprises a pusher plate mount that couples the pusher plate to the rack second end and provides freedom of movement of the pusher plate about one or more axes with regard to the rack.

10. A surgical system, comprising:

a frame assembly comprising a first post, a second post, and a crossbar between the first post and the second post; and a surgical device comprising a ratchet and a lifter plate coupled to the crossbar via the ratchet;

wherein the ratchet comprises a rack comprising a rack first end and a rack second end;

wherein the lifter plate comprises:

a lifter plate first side;

a lifter plate second side opposite the lifter plate first side;

a lifter plate top side coupled to the rack first end; and a plurality of holes that pass through the lifter plate first side and the lifter plate second side; and wherein the ratchet provides ratcheted movement that draws the rack first end and the lifter plate coupled to the rack first end toward the crossbar.

11. The surgical system of claim 10, wherein the lifter plate comprises a lifter plate mount that couples the lifter plate to the rack first end and provides freedom of movement of the lifter plate about one or more axes with regard to the rack.

12. A surgical system, comprising:

a frame assembly comprising a first post, a second post, and a crossbar between the first post and the second post; and a surgical device comprising a ratchet and a lifter plate coupled to the crossbar via the ratchet;

wherein the ratchet comprises a rack comprising a rack first end and a rack second end;

wherein the ratchet provides ratcheted movement that draws the rack first end and the lifter plate coupled to the rack first end toward the crossbar; and wherein the lifter plate comprises:

a lifter plate top side coupled to the rack first end;

a lifter plate bottom side opposite the lifter plate top side;

one or more lifter plate lateral sides between the lifter plate top side and the lifter plate bottom side; and one or more lateral slots that extend into the lifter plate from a respective lifter plate lateral side.

13. The surgical system of claim 12, wherein the lifter plate comprises one or more top slots that extend into the lifter plate from the lifter plate top side.

14. The surgical system of claim 13, wherein the lifter plate comprises one or more spools defined by the one or more lateral slots and the one or more top slots.

15. The surgical system of claim 12, wherein the lifter plate comprises a lift plate mount that couples the lifter plate to the rack first end and provides freedom of movement of the lifter plate about one or more axes with regard to the rack.

16. A surgical system, comprising:

a frame assembly comprising a first post, a second post, and a crossbar between the first post and the second post; and a surgical device comprising a ratchet and a lifter plate coupled to the crossbar via the ratchet;

wherein the ratchet comprises a rack comprising a rack first end and a rack second end;

wherein the ratchet provides ratcheted movement that draws the rack first end and the lifter plate coupled to the rack first end toward the crossbar;

wherein the lifter plate comprises:

a lifter plate top side coupled to the rack first end; and teeth along the lifter plate top side.

17. The surgical system of claim 16, comprising:

a pusher plate coupled to the rack second end; and wherein the ratcheted movement pushes the rack second end and the pusher plate coupled to the rack second end away from the crossbar.

18. The surgical system of claim 17, wherein the pusher plate comprises:

a pusher plate first side coupled to the rack second end;

a pusher plate second side opposite the pusher plate first side; and wherein the pusher plate second side provides a convex surface to engage an anterior chest wall and/or sternum of a patient.

19. The surgical system of claim 17, wherein the pusher plate comprises a pusher plate mount that couples the pusher plate to the rack second end and provides freedom of movement of the pusher plate about one or more axes with regard to the rack.

20. The surgical system of claim 16, wherein the lifter plate comprises a lift plate mount that couples the lifter plate to the rack first end and provides freedom of movement of the lifter plate about one or more axes with regard to the rack.

* * * * *